United States Patent
Hirayama

(10) Patent No.: US 8,668,869 B2
(45) Date of Patent: *Mar. 11, 2014

(54) ANALYZER

(75) Inventor: Hideki Hirayama, Akashi (JP)

(73) Assignee: Sysmex Corporation, Kobe (JP)

( * ) Notice: Subject to any disclaimer, the term of this patent is extended or adjusted under 35 U.S.C. 154(b) by 730 days.

This patent is subject to a terminal disclaimer.

(21) Appl. No.: 12/381,973

(22) Filed: Mar. 18, 2009

(65) Prior Publication Data

US 2009/0259427 A1 Oct. 15, 2009

Related U.S. Application Data

(63) Continuation of application No. 10/890,683, filed on Jul. 14, 2004, now abandoned.

(30) Foreign Application Priority Data

Jul. 16, 2003 (JP) ................................. 2003-197607

(51) Int. Cl.
*G01N 33/00* (2006.01)
(52) U.S. Cl.
USPC .................. 422/67; 422/105; 436/50; 436/55
(58) Field of Classification Search
USPC ................... 422/67, 105; 436/50, 55
See application file for complete search history.

(56) References Cited

U.S. PATENT DOCUMENTS

| 6,391,263 B1 | 5/2002 | Mishima et al. |
| 6,396,518 B1 | 5/2002 | Dow et al. |
| 6,868,308 B2 | 3/2005 | Ito et al. |
| 2002/0103642 A1 | 8/2002 | Asada |
| 2003/0007498 A1 | 1/2003 | Angle et al. |
| 2003/0070498 A1* | 4/2003 | Ohyama et al. ............ 73/863.01 |

FOREIGN PATENT DOCUMENTS

| JP | 08-332180 A | 12/1996 |
| JP | 09-259063 A | 10/1997 |
| JP | 2000-069404 A | 3/2000 |
| JP | 2000-137827 A | 5/2000 |
| JP | 2001-002695 A | 1/2001 |
| JP | 2001-245026 A | 9/2001 |
| JP | 2001-350555 A | 12/2001 |
| JP | 2002-082119 A | 3/2002 |
| JP | 2002-372547 A | 12/2002 |

OTHER PUBLICATIONS

Koga, Naruhisa, "Prompt determination using IC card; Automatic blood cell counter for animals; LC-152," Readout, No. 20, Mar. 2000, Japan, pp. 32-33 (with translation).

* cited by examiner

*Primary Examiner* — Natalia Levkovich
(74) *Attorney, Agent, or Firm* — Brinks Gilson & Lione

(57) ABSTRACT

Analyzers are described that includes a mode selector for selecting one measurement mode from said plurality of measurement modes; a display for displaying a screen; and a display controller for displaying on said screen a picture representing contents of the measurement mode selected by said mode selector.

16 Claims, 12 Drawing Sheets

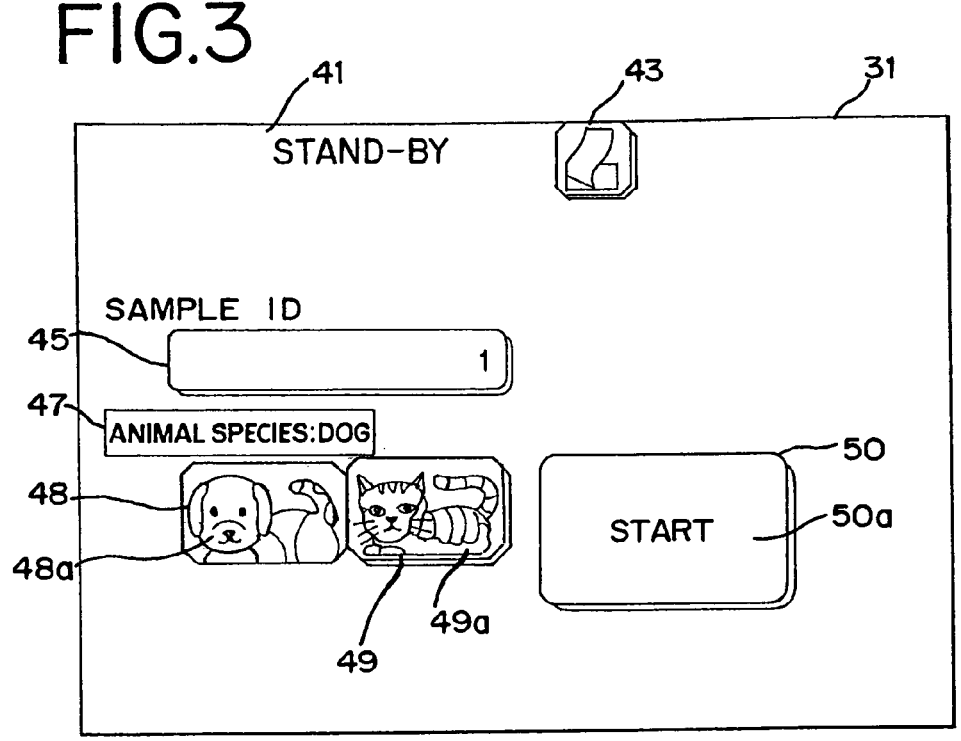
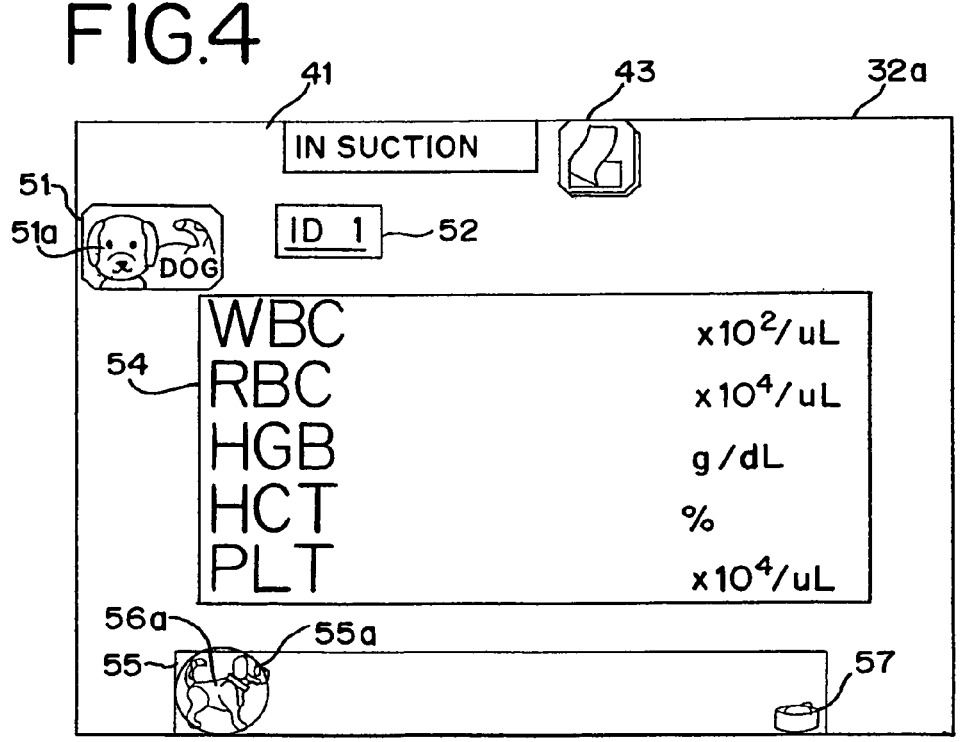

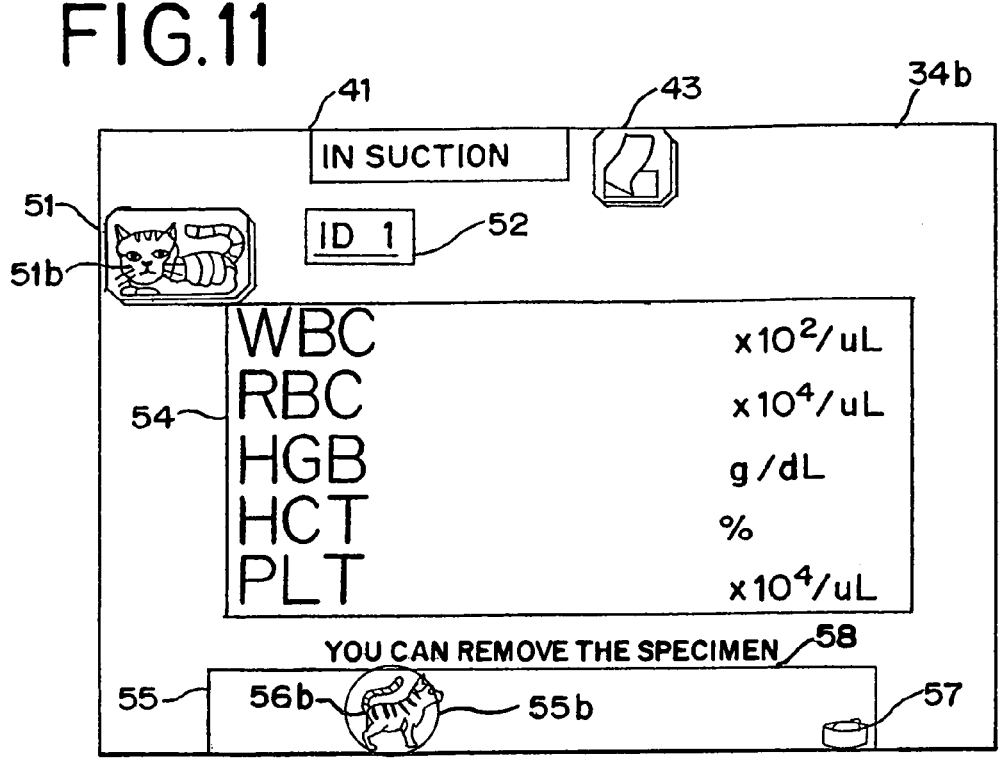
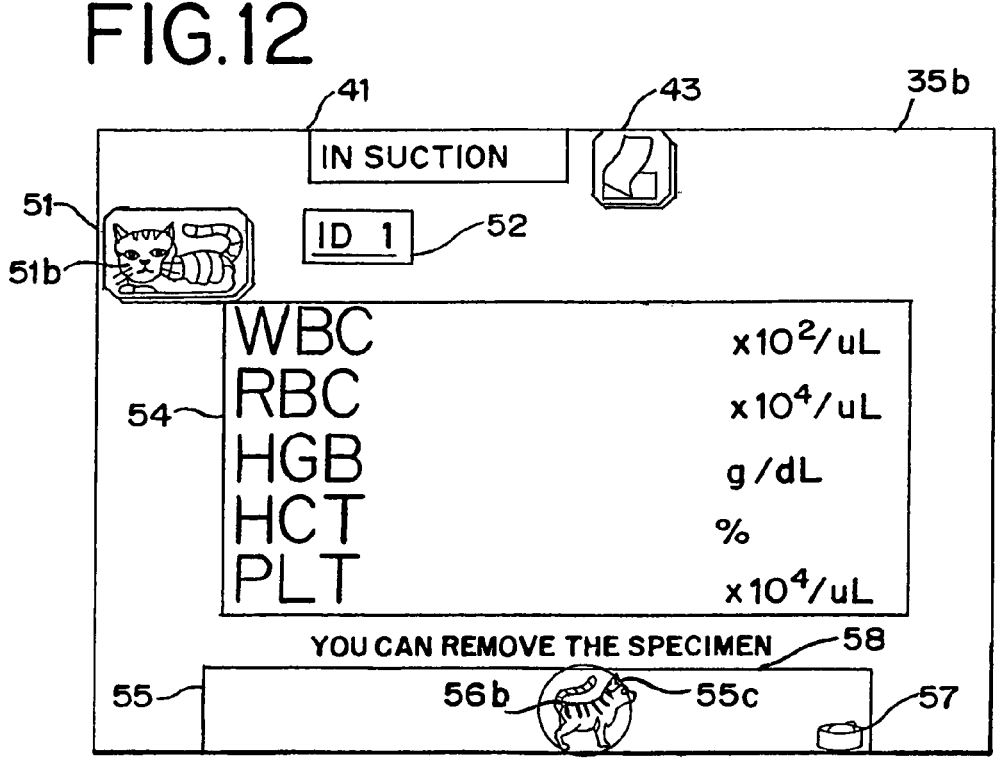

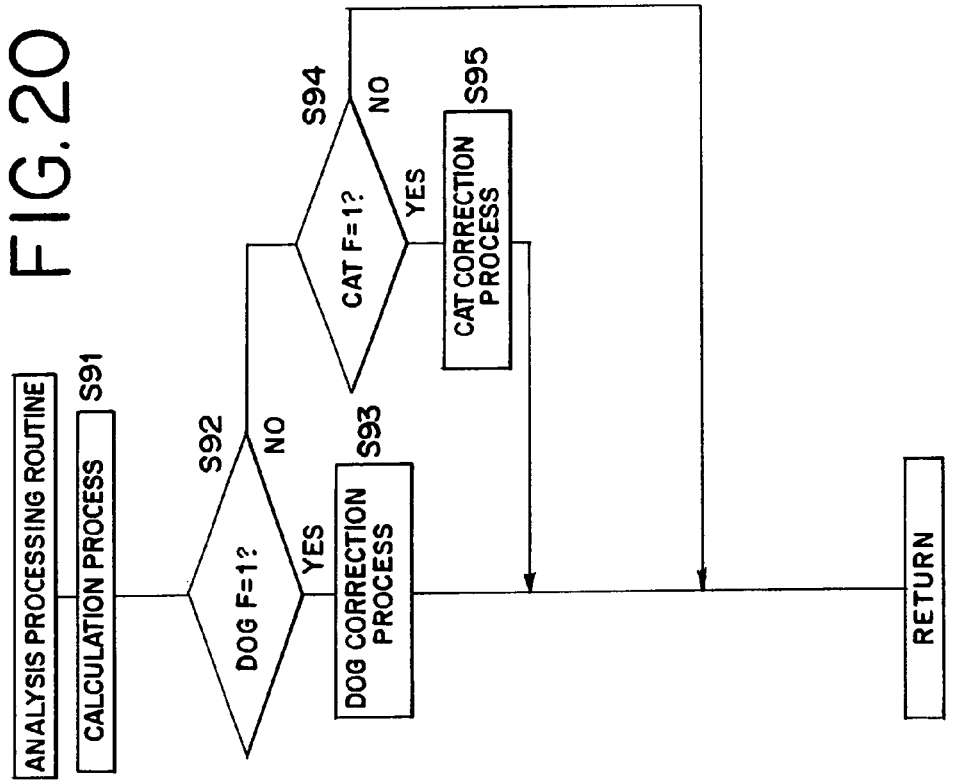
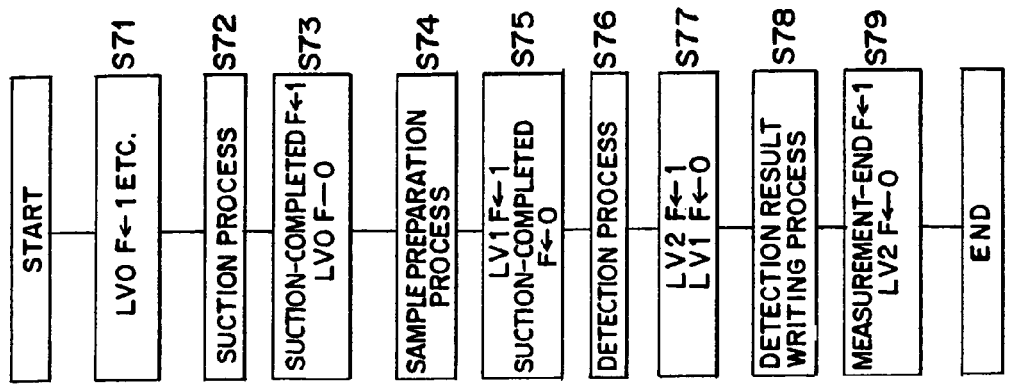

ANALYZER

RELATED APPLICATIONS

This application is a continuation of prior application Ser. No. 10/890,683, filed Jul. 14, 2004 now abandoned, which claims priority under 35 U.S.C. §119 to Japanese Patent Application No. 2003-197607, filed Jul. 16, 2003. The entire contents of both of these documents are incorporated by reference herein.

FIELD OF THE INVENTION

The present invention relates to an analyzer, and more particularly to an analyzer that a user can use easily.

BACKGROUND

A conventional analyzer includes a display and is constructed so as to perform input of commands for starting measurement operations and display of analysis results with the use of this display.

Further, there are conventional analyzer capable of operating in a plurality of measurement modes, and some of such analyzer change the color of start buttons displayed on the display in accordance with the selected measurement mode (for example, see United States Published Patent Application No. 2003/0070498).

Conventional analyzer improve the facility of operation by having such a construction.

For example, the analyzer disclosed in the aforementioned United States Published Patent Application No. 2003/0070498 is such that a user can understand a selected measurement mode if the user memorizes the colors of start buttons and the measurement modes in correspondence. However, a user who is not familiar with operations may not understand what the change in color of the start buttons means, so that the improvement in the facility of operation is not sufficient.

SUMMARY

The scope of the present invention is defined solely by the appended claims, and is not affected to any degree by the statements within this summary.

First analyzer embodying features of the present invention improves facility of operation.

Second analyzer embodying features of the present invention includes a mode selector for selecting one measurement mode from said plurality of measurement modes; a display for displaying a screen; and a display controller for displaying on said screen a picture representing contents of the measurement mode selected by said mode selector.

Third analyzer embodying features of the present invention includes a mode selector for selecting one measurement mode from said plurality of measurement modes; a measurement device for measuring an analyte by successively executing a measurement process composed of a plurality of steps; a monitor means for monitoring a progression of said measurement process; a display; and a display controller for controlling said display so as to change a display image in accordance with the measurement mode selected by said mode selector and the progression monitored by said monitor means.

Fourth analyzer embodying features of the present invention includes a measurement device for measuring an analyte by successively executing a measurement process composed of a plurality of steps; a monitor means for monitoring said measurement process; a memory for storing message that reports a progression of said measurement process; a display for displaying said message; and a display controller for retrieving from said memory a message corresponding to the progression of said measurement process and for displaying said retrieved message on said display.

Fifth analyzer embodying features of the present invention includes a cry generator for generating cries of plural animals; a mode selector for selecting a measurement mode for measuring an animal of one kind from a plurality of measurement modes; and a state monitor means for monitoring a state of said analyzer, wherein said cry generator generates a cry of an animal corresponding to the measurement mode selected by said mode selector when said state monitor means monitors a predetermined state of said analyzer.

BRIEF DESCRIPTION OF THE DRAWINGS

FIG. 3 is a view showing a main screen;

FIG. 4 is a view showing a mid-initial-measurement screen (dog);

FIG. 11 is a view showing a mid-measurement screen (specimen removal) when a cat measurement mode is selected;

FIG. 12 is a view showing a mid-measurement screen (LV1) when a cat measurement mode is selected;

FIG. 19 is a flowchart schematically and generally illustrating a process executed by a measurement operation program;

FIG. 20 is a flowchart illustrating the details of analysis processing routine.

DETAILED DESCRIPTION OF THE EMBODIMENT

Hereafter, a blood analyzer will be described as one example of an analyzer.

Figure 1:
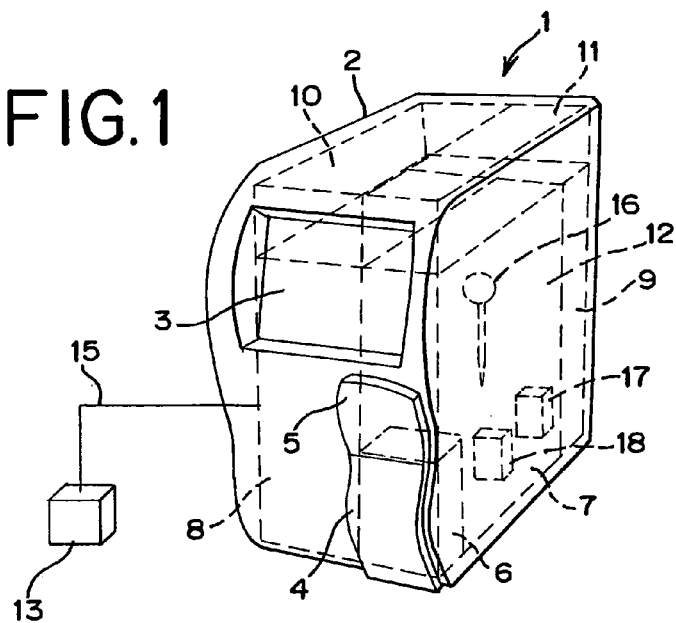
FIG. 1 is a view illustrating a construction of a blood analyzer according to an embodiment of the present invention.

FIG. 1 is a view illustrating a construction of a blood analyzer according to an embodiment of the present invention. A blood analyzer 1 is a blood cell counting device for counting the number of red blood cells, white blood cells, and others of a dog and a cat. Blood analyzer 1 can be operated in a dog measurement mode for measuring the blood of a dog and in a cat measurement mode for measuring the blood of a cat.

Referring to FIG. 1, blood analyzer 1 includes a housing 2, a display 3, a specimen setting panel 4, a press button 5, a controlling substrate section 9, a power section 10, a printer section 11, and a measurement mechanism 12.

Housing 2 houses display 3, controlling substrate section 9, power section 10, printer section 11, and measurement mechanism 12.

Display 3 is a touch-panel type display, which performs display of information and receives input from a user.

Measurement mechanism 12 includes a specimen setting section 6, a specimen processing section 7, and a fluid controlling section 8.

Specimen setting section 6 has an open upper surface, whereby a specimen container can be set into the inside thereof through the upper surface. Specimen setting panel 4 is mounted on specimen setting section 6, and is located outside of housing 2.

Press button 5 is disposed outside of housing 2, and positions specimen setting section 6 by engagement with specimen setting panel 4. When press button 5 is pressed by a user, the engagement implemented by press button 5 is released, and specimen setting section 6 rotates by 45° in the direction of arrow A around axis R integrally with specimen setting panel 4. This provides that the user can set a specimen container (container containing a blood sample) through the upper surface of specimen setting section 6. The user having set the specimen container pushes specimen setting panel 4 to return specimen setting section 6 to the position shown in FIG. 1. Similarly, in removing the specimen container from specimen setting section 6, the user presses press button 5 to rotate specimen setting section 6 by 45° for removing the specimen container.

Specimen processing section 7 includes a suction mechanism 16, a detection section 17, and a mixing chamber 18.

Suction mechanism 16 is a mechanism for sucking a specimen from a specimen container set in specimen setting section 6 and injecting the specimen into detection section 17 and mixing chamber 18, and includes a sucking tube, a motor for moving the sucking tube, and others.

Detection section 17 is a detection section of electric resistance type, and detects an electric signal from blood cells in the specimen. As detection section 17, one can use, for example, the detection section disclosed in the specification of United States Published Patent Application No. 2002/0034824.

Mixing chamber 18 is a container having an open top for mixing a specimen with a reagent.

A reagent container 13 that contains a reagent is connected to fluid controlling section 8 via a tube 15. Fluid controlling section 8 includes a pump for conveying a reagent, a motor for driving the pump, and others, so as to inject and discharge the specimen and the reagent into and from detection section 17 and mixing chamber 18.

Controlling substrate section 9 controls various sections and calculates analysis results. The construction of controlling substrate section 9 will be described later.

Power section 10 converts AC current received from a service AC power source into DC current, and supplies the DC current to controlling substrate section 9, the motors of various sections, and others.

Printer section 11 includes a printer for printing the analysis results and others.

Figure 2:
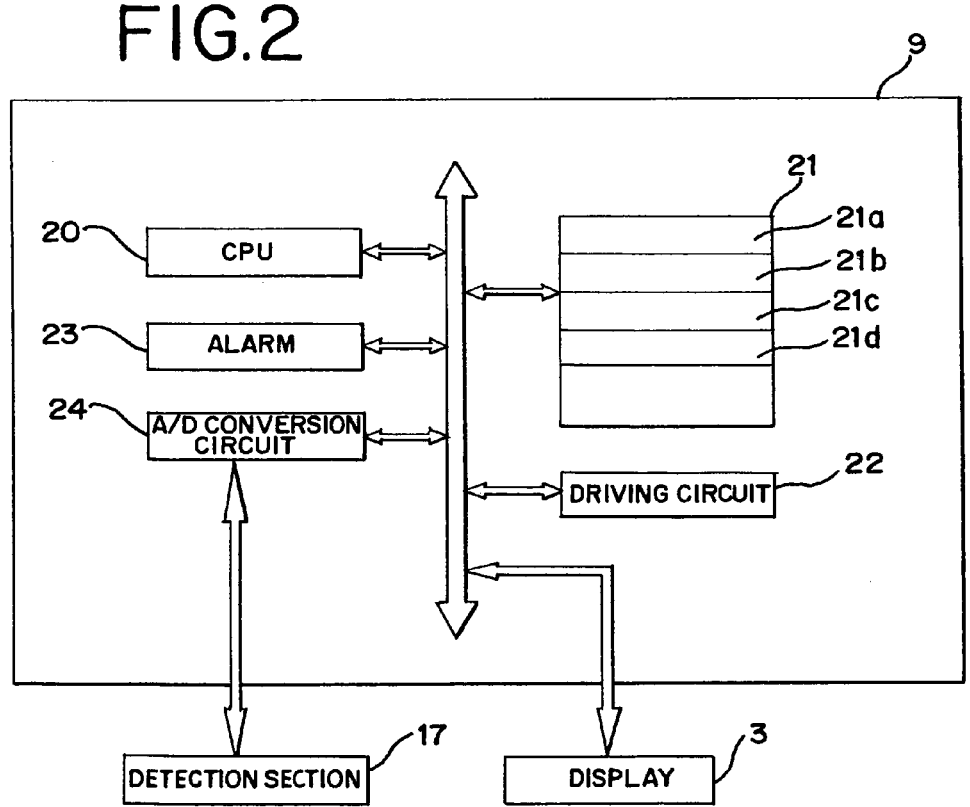
FIG. 2 is a view illustrating a construction of controlling substrate section 9.

FIG. 2 is a view illustrating a construction of controlling substrate section 9. Controlling substrate section 9 includes a CPU 20, a memory 21, a driving circuit 22, an alarm 23, and an A/D conversion circuit 24. Controlling substrate section 9 is connected to display 3.

Memory 21 stores programs, analysis results, and others. As memory 21, one can use, for example, a flash memory (registered trademark). Memory 21 includes area 21$a$, area 21$b$, area 21$c$, area 21$d$, and others.

Area 21$a$ stores application programs for performing overall control including the control of a screen to be displayed on display 3 of blood analyzer 1. Area 21$b$ stores measurement operation programs that perform control of the measurement operation by operating the motors and the like of fluid controlling section 8 and suction mechanism 16. Area 21$c$ and area 21$d$ are areas that the application programs and the measurement operation programs use in common. Area 21$c$ stores various flags, and area 21$d$ stores detection results obtained by digital conversion of the electric signal detected in detection section 17.

Driving circuit 22 receives commands from the measurement operation programs and controls the operation of the motors and the like.

Alarm 23 generates sounds by receiving a command from the application programs.

A/D conversion circuit 24 is a circuit that performs digital conversion of the electric signal obtained in detection section 17. A/D conversion section 24 is connected to detection section 17.

Hereafter, the screen displayed on display 3 will be described.

FIG. 3 is a view illustrating a main screen. A user uses this screen for executing selection of a measurement mode and giving commands for start of the measurement.

Main screen 31 includes an apparatus state display area 41, a print commanding area 43, a specimen number display area 45, an animal species display area 47, a dog selection area 48, a cat selection area 49, and a start button display area 50.

Apparatus state display area 41 is an area that displays the current state of blood analyzer 1 and is, in this view, displaying the letters "stand-by" showing that blood analyzer 1 is in a state capable of starting the measurement.

Print commanding area 43 is an area that displays an icon for commanding printer section 11 to print analysis results and others.

Specimen number display area 45 is an area that displays the specimen number of the specimen to be measured next. In this view, the number "1" is displayed as the specimen number. Here, input of the specimen number is carried out with the use of ten keys (not illustrated) that are displayed when the user touches specimen number display area 45.

Measurement mode display area 47 is an area that displays the selected measurement mode with letters. In this view, the area shows that the dog measurement mode is currently selected.

Dog selection area 48 is an area that displays a switch 48$a$ for selecting the dog measurement mode. When the user touches this switch 48$a$, the dog measurement mode is selected.

Cat selection area 49 is an area that displays a switch 49a for selecting the cat measurement mode. When the user touches this switch 49a, the cat measurement mode is selected.

Here, a picture of a dog and a picture of a cat are drawn in switch 48a and in switch 49a, respectively, so that the user may easily understand which switch should be touched upon.

Start button display area 50 is an area that displays start button 50a for giving orders of the start of measurement.

FIG. 4 is a view illustrating a mid-initial-measurement screen (dog) that is displayed on display 3 immediately after the user touches start button display area 50 (FIG. 3) when the dog measurement mode is selected. Here, the areas having the same functions as the areas described in FIG. 3 will be denoted with the same symbols, and a description thereof will be omitted.

Mid-initial-measurement screen (dog) 32a includes an apparatus state display area 41, a print commanding area 43, a measurement mode display area 51, a specimen number display area 52, an analysis result display area 54, and a progression display area 55.

Apparatus state display area 41 is currently displaying the letters "in suction" showing that suction mechanism 16 is sucking the specimen.

Measurement mode display area 51 is an area that displays the selected measurement mode with a picture. Measurement mode display area 51 is currently displaying a dog picture 51a, showing that the dog measurement mode is selected. Here, dog picture 51a includes the letters "Dog", which make the selected measurement mode more easily understand able.

Specimen number display area 52 is an area that displays the specimen number (ID) of the specimen in measurement. In this view, the number "1" is displayed as an ID.

Analysis result display area 54 is an area that displays the analysis results of the specimen. In mid-initial-measurement screen 32a, this area displays only the measurement items and the units, and does not display the analysis results.

Progression display area 55 is an area that displays the progression of the measurement. In mid-initial-measurement screen 32a, progression display area 55 displays a dog picture 56a and a food picture 57, where dog picture 56a is displayed at the leftmost position 55a of progression display area 55.

Here, dog pictures 51a and 56a are stored in area 21a of memory 21 (FIG. 2).

Figure 5:
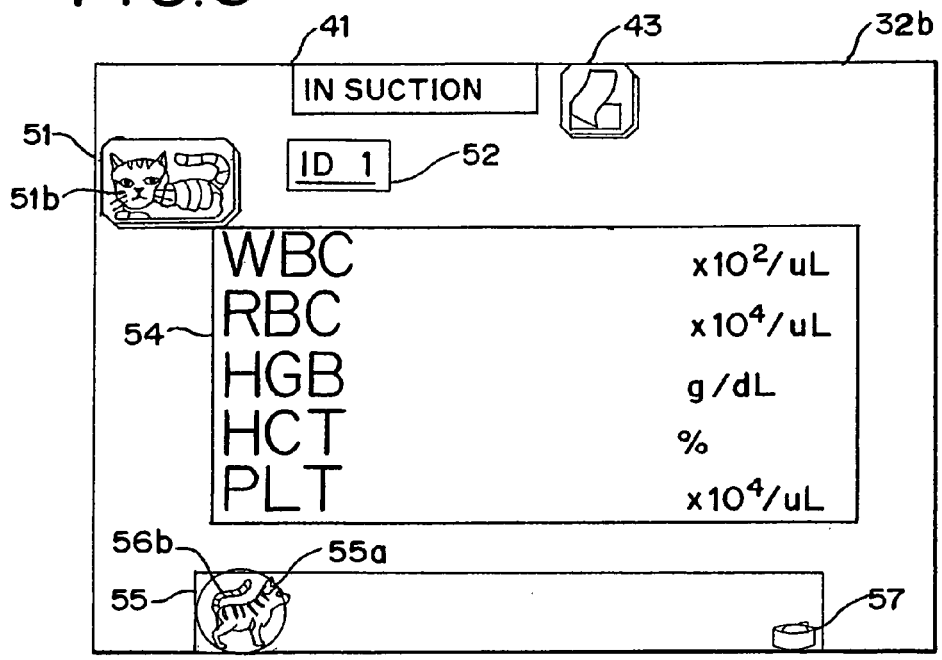
FIG. 5 is a view showing a mid-initial-measurement screen (cat)

FIG. 5 is a view illustrating a mid-initial-measurement screen (cat) that is displayed on display 3 immediately after the user touches start button display area 50 when the cat measurement mode is selected.

Mid-initial-measurement screen (cat) 32b includes an apparatus state display area 41, a print commanding area 43, a measurement mode display area 51, a specimen number display area 52, an analysis result display area 54, and a progression display area 55.

Measurement mode display area 51 is currently displaying a cat picture 51b, showing that the cat measurement mode is selected. Here, cat picture 51b includes the letters "Cat", which make the selected measurement mode more easily understand able.

In mid-initial-measurement screen 32b, progression display area 55 displays a cat picture 56b and a food picture 57, where cat picture 56b is displayed at the leftmost position 55a of progression display area 55.

Here, cat pictures 51b and 56b are stored in area 21a of memory 21 (FIG. 2).

Figure 6:
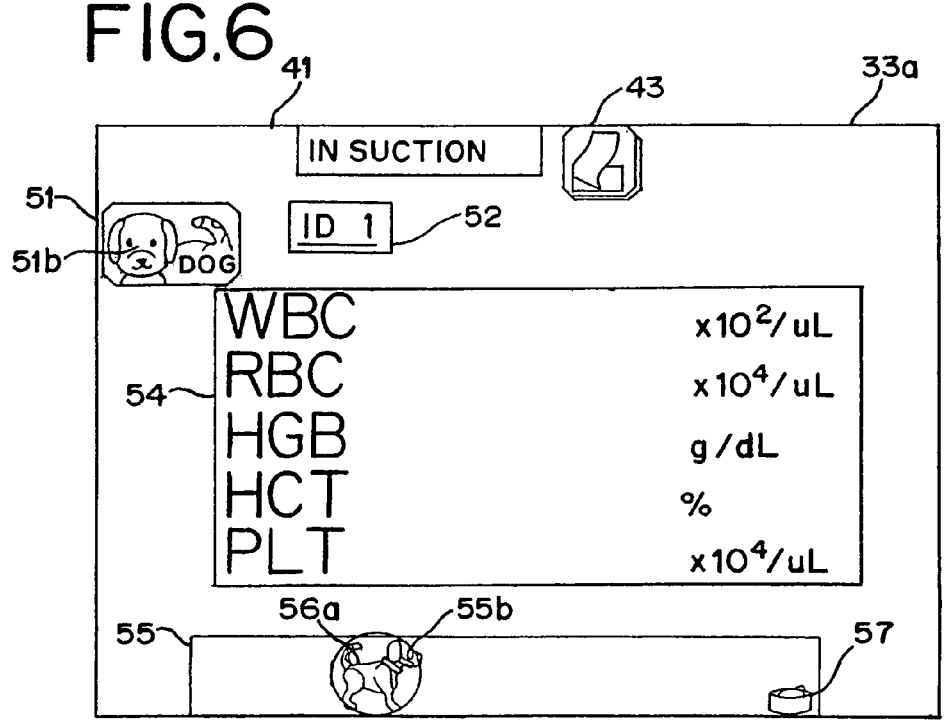
FIG. 6 is a view showing a mid-measurement screen (LV0) when a dog measurement mode is selected.

FIG. 6 is a view illustrating a mid-measurement screen (LV0) that is displayed subsequent to mid-initial-measurement screen 32a (FIG. 4) during the measurement operation when the dog measurement mode is selected.

Mid-measurement screen (LV0) 33a includes an apparatus state display area 41, a print commanding area 43, a measurement mode display area 51, a specimen number display area 52, an analysis result display area 54, and a progression display area 55.

Dog picture 56a is displayed at a position 55b closer to food 57 as compared with the case of mid-initial-measurement screen (dog) 32a.

Figure 7:
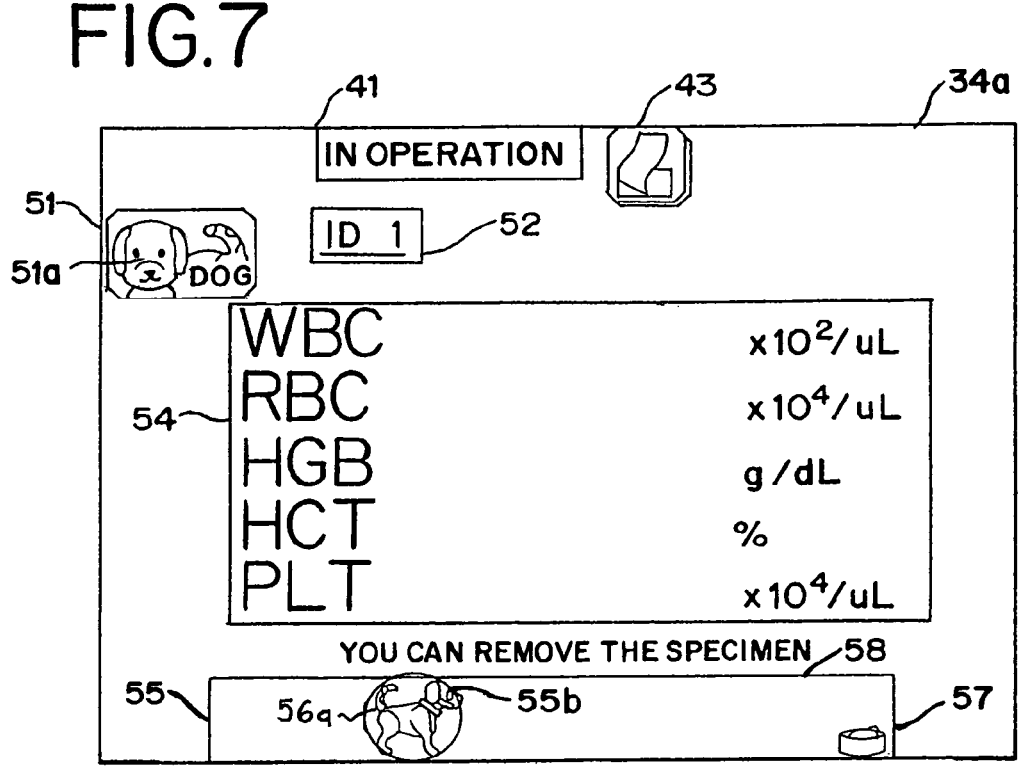
FIG. 7 is a view showing a mid-measurement screen (specimen removal) when a dog measurement mode is selected.

FIG. 7 is a view illustrating a mid-measurement screen (specimen removal) that is displayed subsequent to mid-measurement screen (LV0) 33a (FIG. 6) during the measurement operation when the dog measurement mode is selected.

Mid-measurement screen (specimen removal) 34a includes an apparatus state display area 41, a print commanding area 43, a measurement mode display area 51, a specimen number display area 52, an analysis result display area 54, a progression display area 55, and a specimen removal notification area 58.

Apparatus state display area 41 is currently displaying the letters "in operation" showing that blood analyzer 1 is performing operations such as sample preparation and detection after suction mechanism 16 has finished suction of the specimen.

Specimen removal notification area 58 is an area that notifies the user that the user can remove the specimen container from specimen setting section 6 by pressing press button 5 because suction mechanism 16 has finished suction of the specimen. Specimen removal notification area 58 is displaying the letters "you can remove the specimen".

This provides that the user can instantly understand that the analyzer has been brought into a state such that the specimen container can be removed from specimen setting section 6. Therefore, the user can remove the specimen container at the earliest possible timing after the start of the measurement, so that the user can immediately start the next work.

Dog picture 56a is displayed at the same position 55b as in the case of mid-measurement screen (LV0) 33a (FIG. 6).

Figure 8:
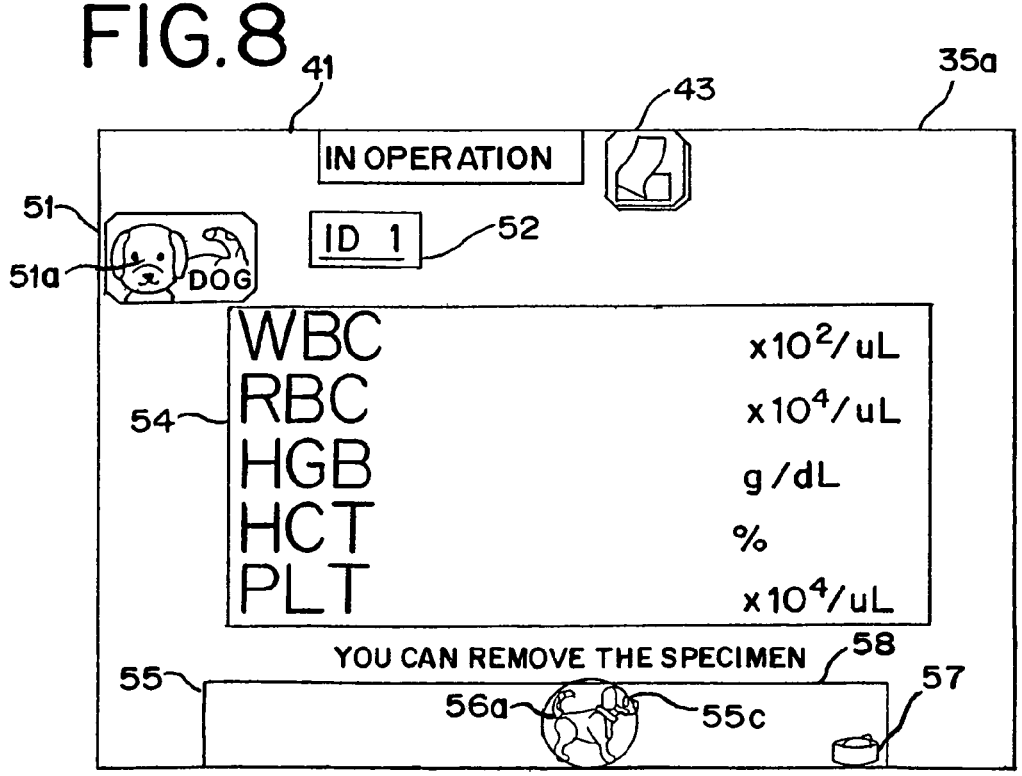
FIG. 8 is a view showing a mid-measurement screen (LV1) when a dog measurement mode is selected.

FIG. 8 is a view illustrating a mid-measurement screen (LV1) that is displayed subsequent to mid-measurement screen (specimen removal) 34a (FIG. 7) during the measurement operation when the dog measurement mode is selected.

Mid-measurement screen (LV1) 35a includes an apparatus state display area 41, a print commanding area 43, a measurement mode display area 51, a specimen number display area 52, an analysis result display area 54, a progression display area 55, and a specimen removal notification area 58.

Dog picture 56a is displayed at a position 55c closer to food 57 as compared with the case of mid-measurement screen (specimen removal) 34a.

Figure 9:
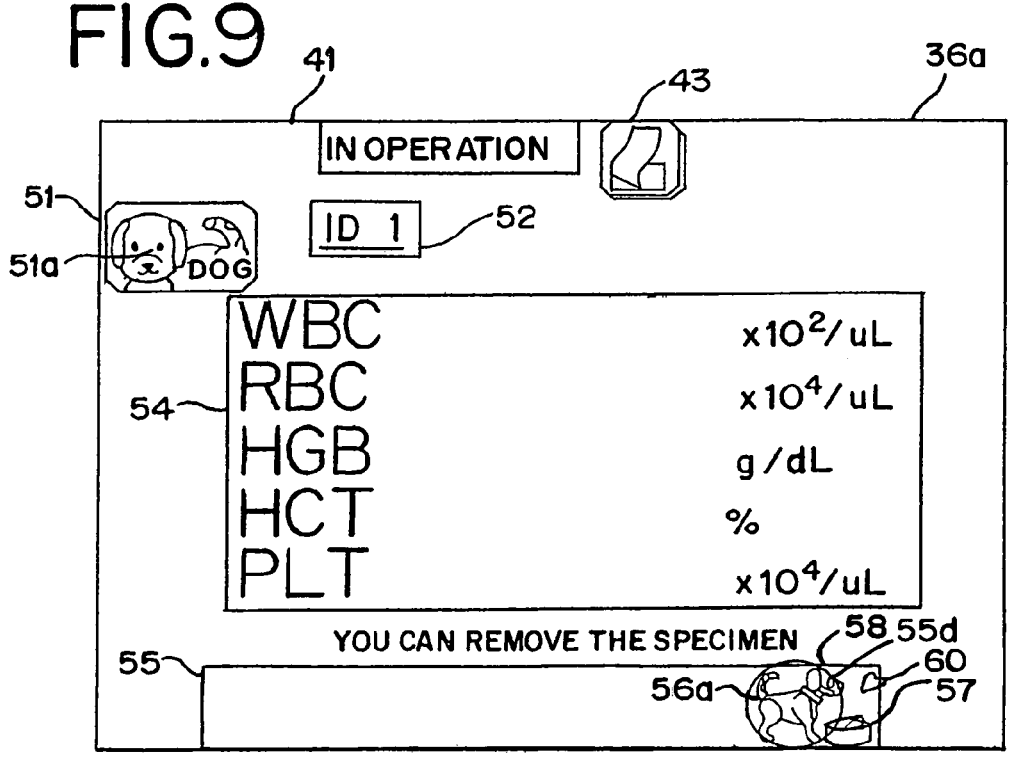
FIG. 9 is a view showing a mid-measurement screen (LV2) when a dog measurement mode is selected.

FIG. 9 is a view illustrating a mid-measurement screen (LV2) that is displayed subsequent to mid-measurement screen (LV1) 35a (FIG. 8) during the measurement operation when the dog measurement mode is selected.

Mid-measurement screen (LV2) 36a includes an apparatus state display area 41, a print commanding area 43, a measurement mode display area 51, a specimen number display area 52, an analysis result display area 54, a progression display area 55, and a specimen removal notification area 58.

Dog picture 56a is displayed at a position 55d immediately close to food picture 57. Further, a heart picture 60 is displayed immediately close to dog picture 56a. These pictures show that the dog is in a state being capable of having the food and is rejoicing. This provides that the user can recognize that the measurement operation performed by measurement mechanism 12 has been finished, and recognize that the analysis results will be displayed soon. In other words, heart picture 60 is a picture for notifying the user that the measurement operation has ended (end notification picture).

Figure 10:
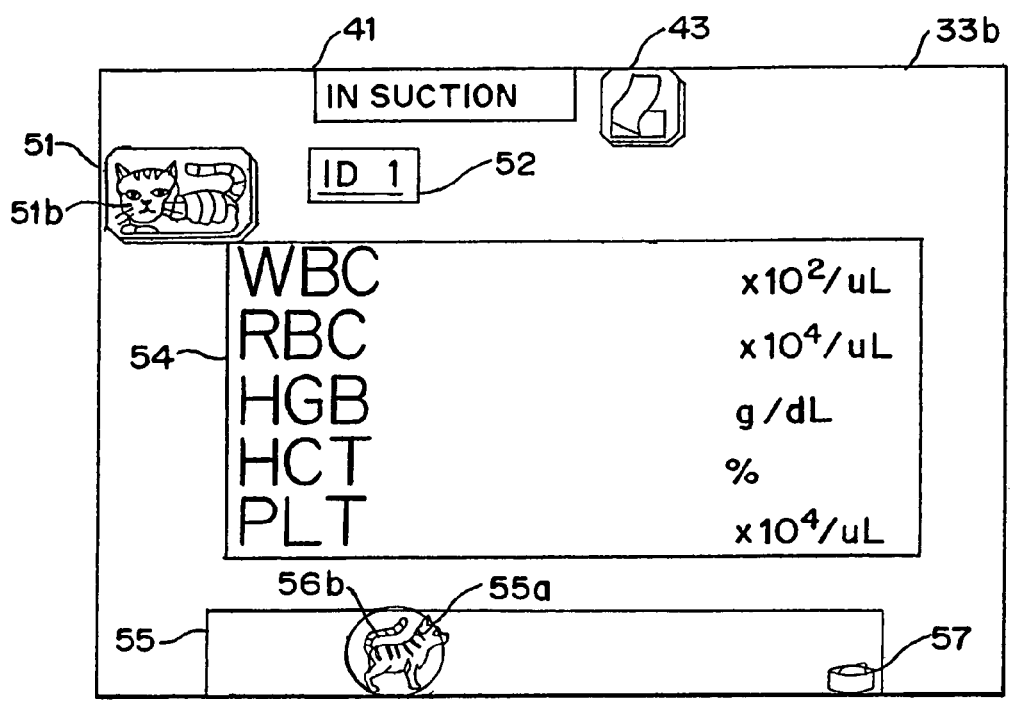
FIG. 10 is a view showing a mid-measurement screen (LV0) when a cat measurement mode is selected.

FIG. 10 is a view illustrating a mid-measurement screen (LV0) that is displayed subsequent to mid-initial-measurement screen 32b (FIG. 5) during the measurement operation when the cat measurement mode is selected.

Mid-measurement screen (LV0) 33b includes an apparatus state display area 41, a print commanding area 43, a measurement mode display area 51, a specimen number display area 52, an analysis result display area 54, and a progression display area 55.

Cat picture 56b is displayed at a position 55b closer to food 57.as compared with the case of mid-initial-measurement screen (cat) 32b.

FIG. 11 is a view illustrating a mid-measurement screen (specimen removal) that is displayed subsequent to mid-measurement screen (LV0) 33b (FIG. 10) during the measurement operation when the cat measurement mode is selected.

Mid-measurement screen (specimen removal) 34b includes an apparatus state display area 41, a print commanding area 43, a measurement mode display area 51, a specimen number display area 52, an analysis result display area 54, a progression display area 55, and a specimen removal notification area 58.

Apparatus state display area 41 is currently displaying the letters "in operation" showing that blood analyzer 1 is performing operations such as sample preparation and detection after suction mechanism 16 has finished suction of the specimen.

Specimen removal notification area 58 is an area that notifies the user that the user can remove the specimen container from specimen setting section 6 by pressing press button 5 because suction mechanism 16 has finished suction of the specimen. Specimen removal notification area 58 is displaying the letters "you can remove the specimen".

Cat picture 56b is displayed at the same position 55b as in the case of mid-measurement screen (LV0) 33b (FIG. 10).

FIG. 12 is a view illustrating a mid-measurement screen (LV1) that is displayed subsequent to mid-measurement screen (specimen removal) 34b (FIG. 11) during the measurement operation when the cat measurement mode is selected.

Mid-measurement screen (LV1) 35b includes an apparatus state display area 41, a print commanding area 43, a measurement mode display area 51, a specimen number display area 52, an analysis result display area 54, a progression display area 55, and a specimen removal notification area 58.

Cat picture 56b is displayed at a position 55c closer to food 57 as compared with the case of mid-measurement screen (specimen removal) 34b.

Figure 13:
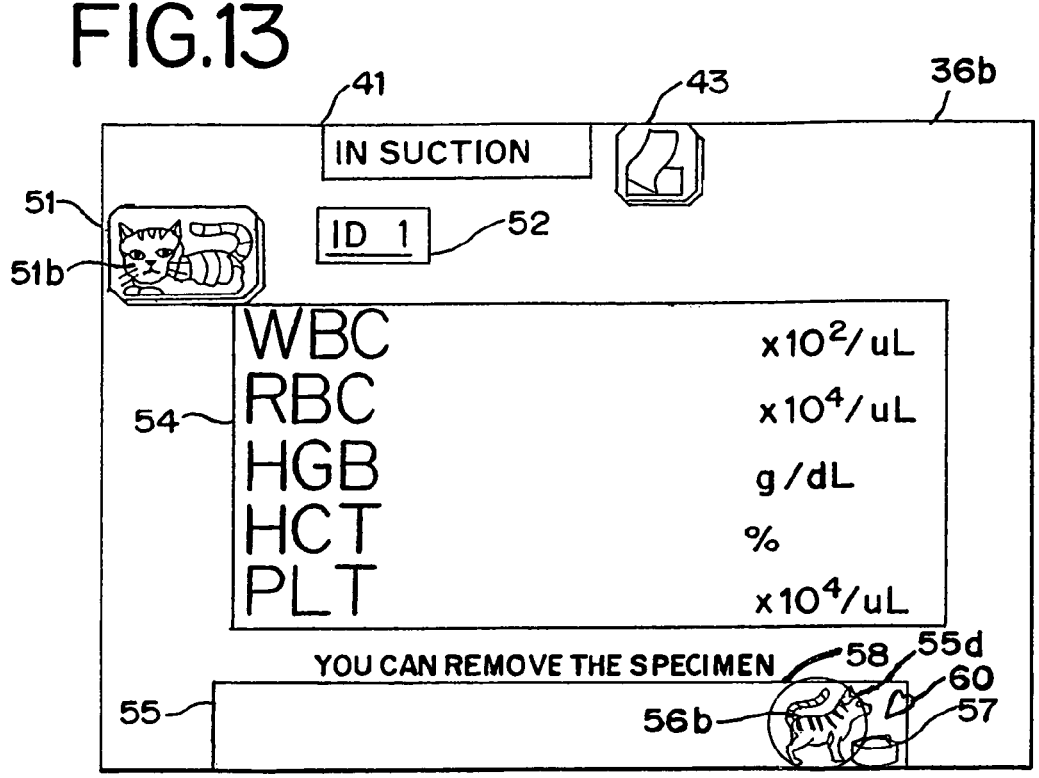
FIG. 13 is a view showing a mid-measurement screen (LV2) when a cat measurement mode is selected.

FIG. 13 is a view illustrating amid-measurement screen (LV2) that is displayed subsequent to mid-measurement screen (LV1) 35b (FIG. 12) during the measurement operation when the cat measurement mode is selected.

Mid-measurement screen (LV2) 36b includes an apparatus state display area 41, a print commanding area 43, a measurement mode display area 51, a specimen number display area 52, an analysis result display area 54, a progression display area 55, and a specimen removal notification area 58.

Cat picture 56b is displayed at a position 55d immediately close to food picture 57. Further, a heart picture 60 is displayed immediately close to cat picture 56a. These pictures show that the cat is in a state being capable of having the food and is rejoicing. This provides that the user can recognize that the measurement operation performed by measurement mechanism 12 has been finished, and recognize that the analysis results will be displayed soon. In other words, heart picture 60 is a picture for notifying the user that the measurement operation has ended.

As shown in FIGS. 4 to 13, progression display area 55 displays dog picture 56a when the dog measurement mode is selected, and displays cat picture 56b when the cat measurement mode is selected. This provides that the user can confirm the progression of the measurement and simultaneously confirm the selected measurement mode. Progression display area 55 is an area to which the user pays particular attention for confirming the progression of the measurement. Therefore, by displaying pictures representing the measurement modes in this area, the user can confirm the measurement modes without being particularly conscious.

The user can confirm the selected measurement mode by looking at a predetermined area of display 3 at any timing during the measurement operation.

Figure 14:
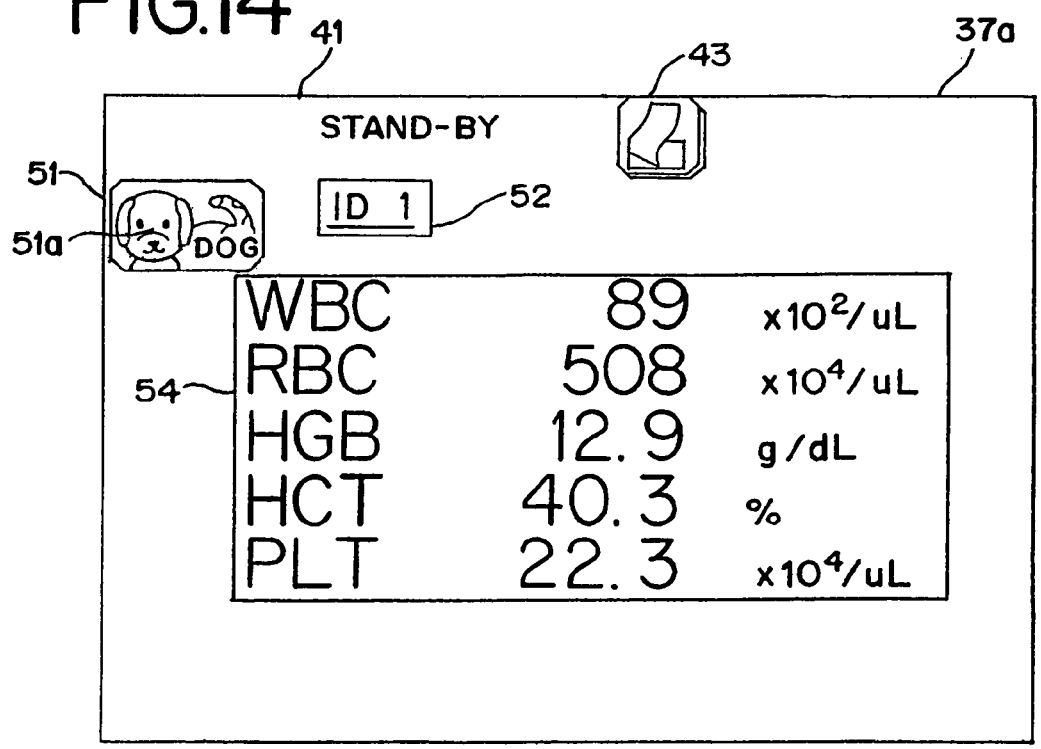
FIG. 14 is a view showing an analysis result screen (dog)

FIG. 14 is a view illustrating an analysis result screen (dog) that is displayed subsequent to mid-measurement screen (LV2) 36a (FIG. 9) when the dog measurement mode is selected.

Analysis result screen (dog) 37a includes an apparatus state display area 41, a print commanding area 43, a measurement mode display area 51, a specimen number display area 52, and an analysis result display area 54.

Apparatus state display area 41 shows that blood analyzer 1 is in a state being capable of starting the measurement, i.e. in a "stand-by" state.

Measurement mode display area 51 is displaying dog picture 51a.

Analysis result display area 54 is displaying the analysis results calculated by CPU 20 (FIG. 2).

Figure 15:
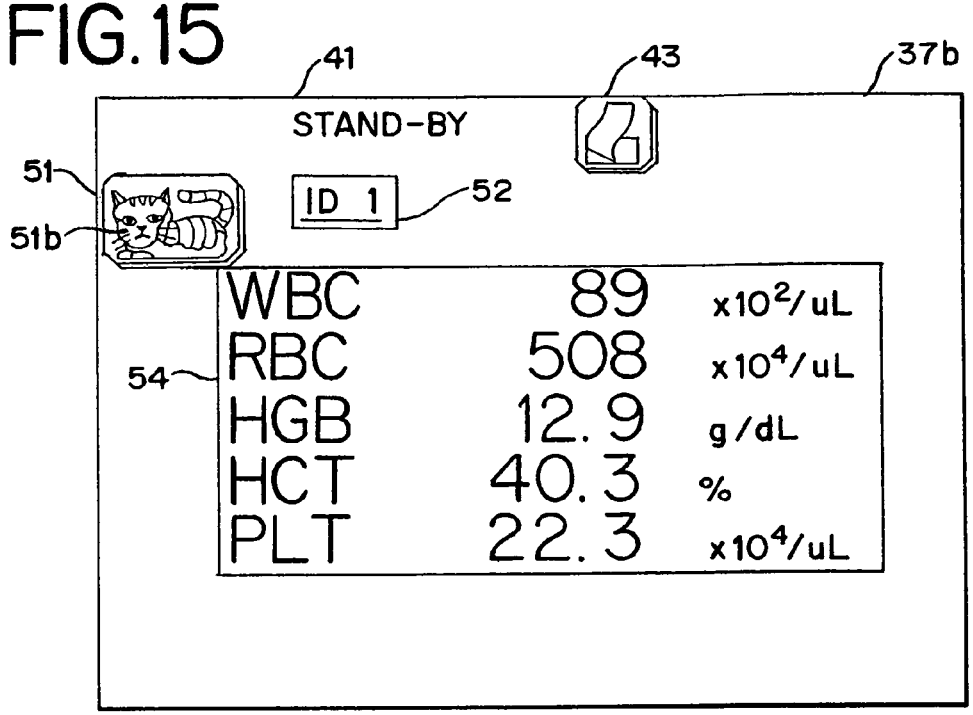
FIG. 15 is a view showing an analysis result screen (cat)

FIG. 15 is a view illustrating an analysis result screen (cat) that is displayed subsequent to mid-measurement screen (LV2) 36b (FIG. 13) when the cat measurement mode is selected.

Analysis result screen (cat) 37b includes an apparatus state display area 41, a print commanding area 43, a measurement mode display area 51, a specimen number display area 52, and an analysis result display area 54.

Apparatus state display area 41 shows that blood analyzer 1 is in a state being capable of starting the measurement, i.e. in a "stand-by" state.

Measurement mode display area 51 is displaying cat picture 51b.

Analysis result display area 54 is displaying the analysis results calculated by CPU 20 (FIG. 2).

Next, operation of blood analyzer 1 will be described with reference to FIGS. 16 to 21.

Figure 16:
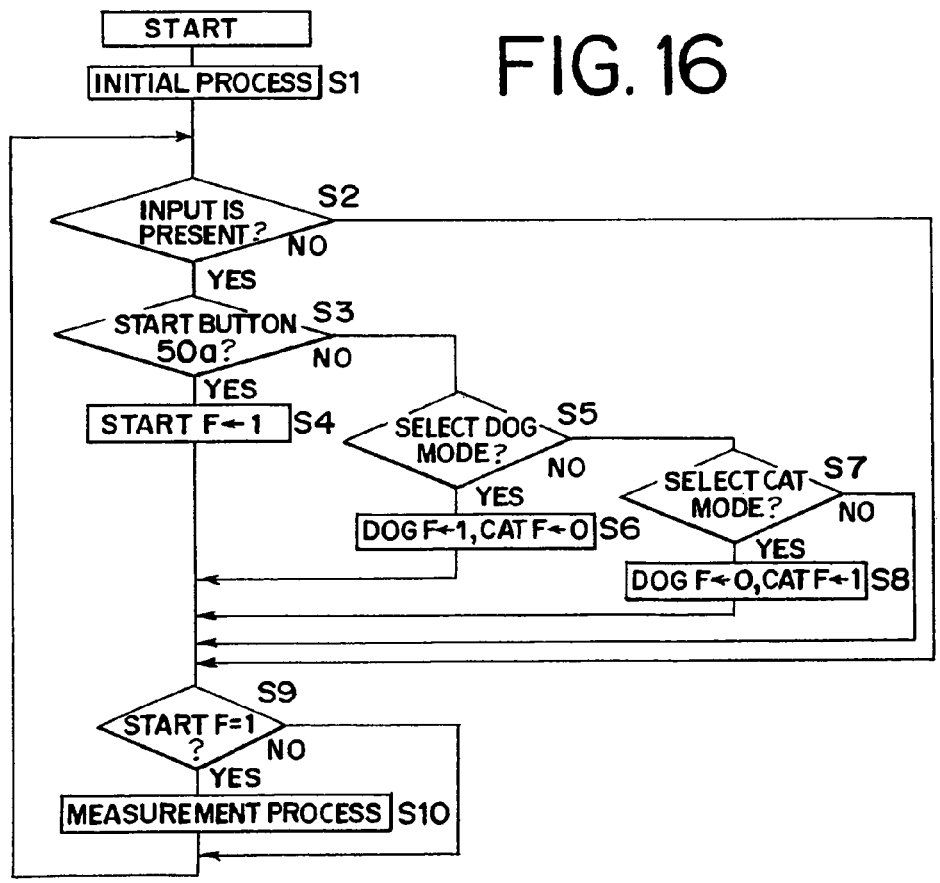
FIG. 16 is a flowchart schematically and generally illustrating a process executed by an application program.

FIG. 16 is a flowchart schematically and generally showing a process executed by an application program stored in area 21a of memory 21.

In step S1, an initial process is carried out. This process executes a process of allowing display 3 to display main screen 31 (FIG. 3), a process of setting the start flag (startF) to be "0", a process of setting the dog flag (dogF) to be "1", and a process of setting the cat flag (catF) to be "0".

In step S2, a process of determining whether there has been an input from display 3 or not is executed. If there has been an input, the procedure goes to step. S3, while if there has not been an input, the procedure goes to step S9.

In step S3, a process of determining whether the input is an input into area 50 or not is executed. In other words, in step S3, a process of determining whether the input is an input of start button 50a or not is executed. If the input is an input of start button 50*a*, the procedure goes to step S4, while if the input is not an input of start button 50*a*, the procedure goes to step S5.

In step S4, a process of setting the start flag to be "1" is executed.

In step S5, a process of determining whether the input is an input of switch 48*a* or not is executed. In other words, in step S5, a process of determining whether a dog mode has been selected or not is executed. If the dog mode is selected, the procedure goes to step S6, while if the dog mode is not selected, the procedure goes to step S7.

In step S6, a process of setting the dog flag to be "1" and setting the cat flag to be "0" is executed. This process selects the dog mode.

In step S7, a process of determining whether the input is an input of switch 49*a* or not is executed. In other words, in step S7, a process of determining whether a cat mode has been selected or not is executed. If, the cat mode is selected, the procedure goes to step S8, while if the cat mode is not selected, the procedure goes to step S9.

In step S8, a process of setting the dog flag to be "0" and setting the cat flag to be "1" is executed. This process selects the cat mode.

In step S9, a process of determining whether the start flag is "1" or not is executed. If the start flag is "1", the procedure goes to step S10, while if the start flag is not "1", the procedure goes to step S2.

In step S10, a measurement process is executed. The details of the measurement process are shown in FIG. 17.

The processes from step S2 to step S10 are repeatedly executed.

Figure 17:
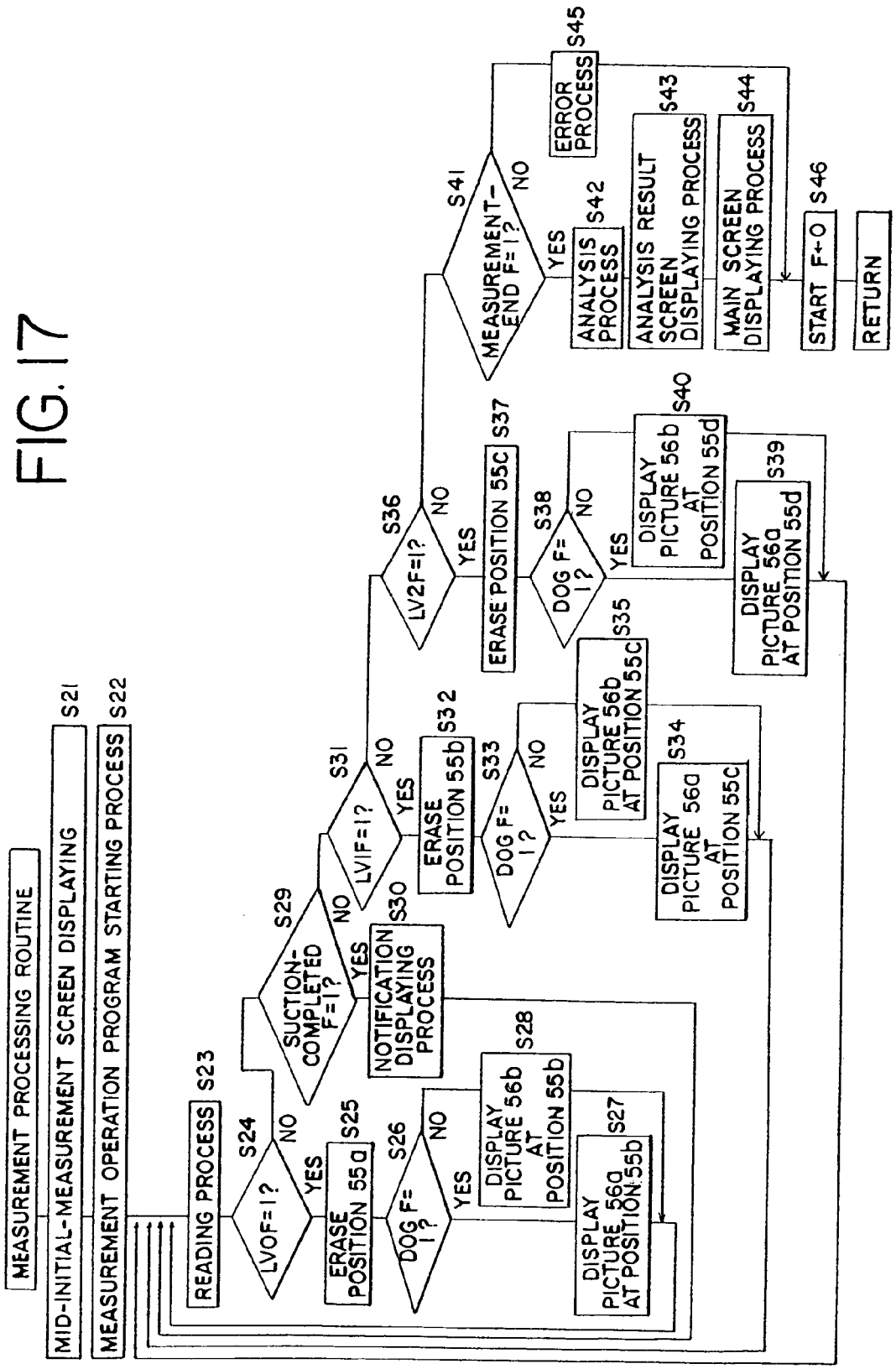
FIG. 17 is a flowchart illustrating the details of a measurement processing routine.

With reference to FIG. 17, the contents of the measurement process in step S10 will be described.

FIG. 17 is a flowchart showing the details of a measurement processing routine.

Figure 18:
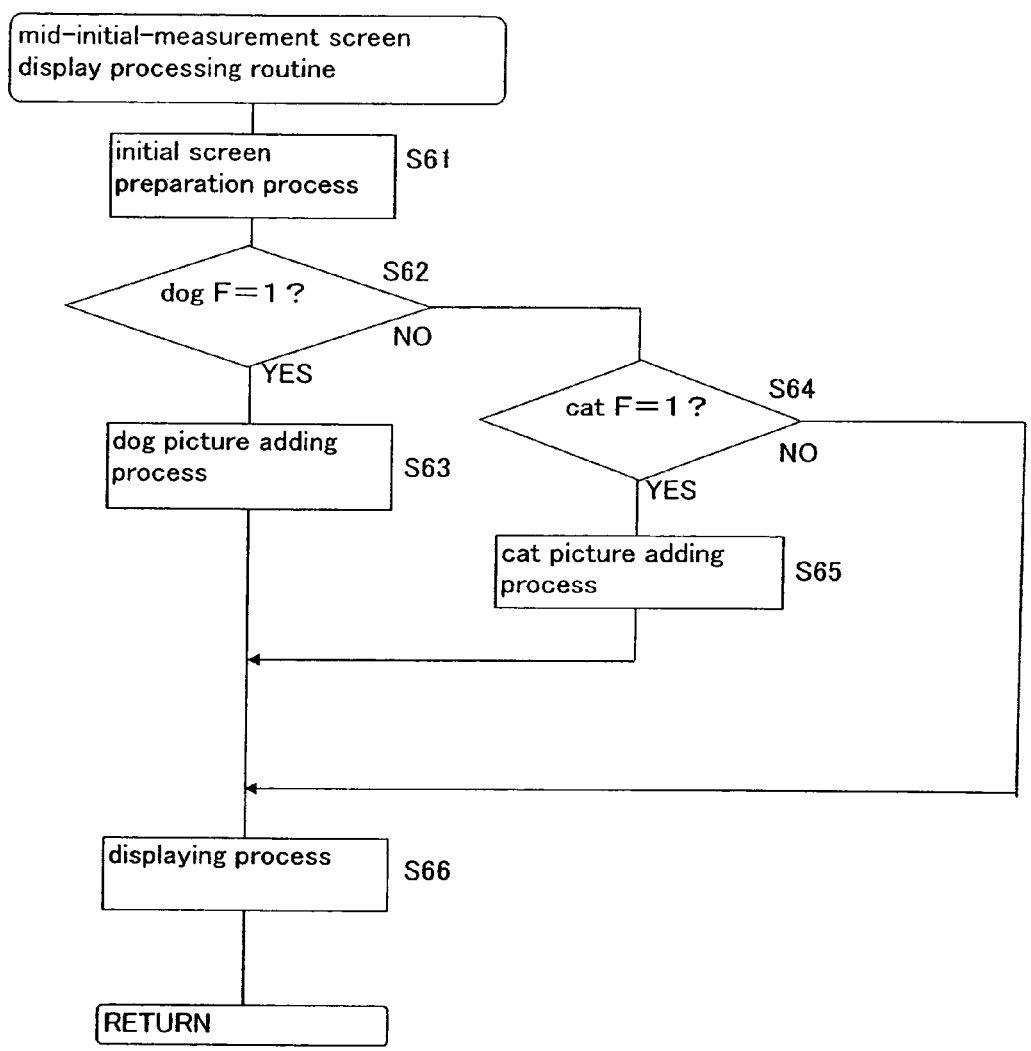
FIG. 18 is a flowchart illustrating the details of a mid-initial-measurement screen display processing routine.

In step S21, a process of allowing display 3 to display a mid-initial-measurement screen (dog) 32*a* (FIG. 4) or a mid-initial-measurement screen (cat) 32*b* (FIG. 5) is executed. By this process, if the dog mode is selected, the mid-initial-measurement screen (dog) 32*a* is displayed on display 3, while if the cat mode is selected, the mid-initial-measurement screen (cat) 32*b* is displayed on display 3. The details of this process are shown in FIG. 18.

In step S22, a process of starting a measurement operation program stored in area 21*b* of memory 21 is executed. The measurement operation program controls operation of the motors and the like of fluid controlling section 8 and suction mechanism 16, and sets the LV0 flag (LV0F), suction-completed flag (suction-completedF), LV1 flag (LV1F), LV2 flag (LV2F), and measurement-end flag (measurement-endF). The processing procedure carried out by the measurement operation program is shown in FIG. 19. Hereafter, the process carried out by the application program and the processes carried out by the measurement operation program are executed in parallel.

In step S23, a reading process is executed. The reading process is a process of reading the contents of the flags each time after a predetermined period of time passes.

In step S24, a process of determining whether the LV0 flag is "1" or not is executed. If the LV0 flag is "1", the procedure goes to step S25, while if the LV0 flag is not "1", the procedure goes to step S29.

In step S25, a process of erasing dog picture 56*a* or cat picture 56*b* from position 55*a* in mid-initial-measurement screen (dog) 32*a* (FIG. 4) or in mid-initial-measurement screen (cat) 32*b* (FIG. 5) is executed. Namely, a process of initializing the display of position 55*a* is executed.

In step S26, a process of determining whether the dog flag is "1" or not is executed. If the dog flag is "1", the procedure goes to step S27, while if the dog flag is not "1", the procedure goes to step S28.

In step S27, a process of displaying dog picture 56*a* at position 55*b* is executed. By this process, mid-measurement screen (LV0) 33*a* (FIG. 6) is displayed on display 3.

In step S28, a process of displaying cat picture 56*b* at position 55*b* is executed. By this process, mid-measurement screen (LV0) 33*b* (FIG. 10) is displayed on display 3.

In step S29, a process of determining whether the suction-completed flag is "1" or not is executed. If the suction-completed flag is "1", the procedure goes to step S30, while if the suction-completed flag is not "1", the procedure goes to step S31.

In step S30, a process of displaying the letters "you can remove the specimen" in specimen removal notification area 58 and generating a sound for warning the user from alarm 23 is executed. Further, in step S30, a process of changing the letters "in suction" in apparatus state display area 41 to the letters "in operation" is executed. By this process, mid-measurement screen (specimen removal) 34*a* (FIG. 7) or mid-measurement screen (specimen removal) 34*b* (FIG. 11) is displayed on display 3.

In step S31, a process of determining whether the LV1 flag is "1" or not is executed. If the LV1 flag is "1", the procedure goes to step S32, while if the LV1 flag is not "1", the procedure goes to step S36.

In step S32, a process of erasing dog picture 56*a* or cat picture 56*b* from position 55*b* in mid-measurement screen (specimen removal) 34*a* (FIG. 7) or in mid-measurement screen (specimen removal) 34*b* (FIG. 11) is executed. Namely, a process of initializing the display of position 55*b* is executed.

In step S33, a process of determining whether the dog flag is "1" or not is executed. If the dog flag is "1", the procedure goes to step S34, while if the dog flag is not "1", the procedure goes to step S35.

In step S34, a process of displaying dog picture 56*a* at position 55*c* is executed. By this process, mid-measurement screen (LV1) 35*a* (FIG. 8) is displayed on display 3.

In step S35, a process of displaying cat picture 56*b* at position 55*c* is executed. By this process, mid-measurement screen (LV1) 35*b* (FIG. 12) is displayed on display 3.

In step S36, a process of determining whether the LV2 flag is "1" or not is executed. If the LV2 flag is "1", the procedure goes to step S37, while if the LV2 flag is not "1", the procedure goes to step S41.

In step S37, a process of erasing dog picture 56*a* from position 55*c* in mid-measurement screen (LV1) 35*a* (FIG. 8) or in mid-measurement screen (LV1) 35*b* (FIG. 12) is executed. Namely, a process of initializing the display of position 55*c* is executed.

In step S38, a process of determining whether the dog flag is "1" or not is executed. If the dog flag is "1", the procedure goes to step S39, while if the dog flag is not "1", the procedure goes to step S40.

In step S39, a process of displaying dog picture 56*a* at position 55*d* and displaying heart picture 60 at a position immediately close to dog picture 56*a* is executed. By this process, mid-measurement screen (LV2) 36*a* (FIG. 9) is displayed on display 3.

In step S40, a process of displaying cat picture 56*b* at position 55*d* and displaying heart picture 60 at a position immediately close to cat picture 56*b* is executed. By this process, mid-measurement screen (LV2) 36*b* (FIG. 13) is displayed on display 3.

In step S41, a process of determining whether the measurement-end flag is "1" or not is executed. If the measurement-end flag is "1", the procedure goes to step S42, while if the measurement-end flag is not "1", the procedure goes to step S45.

In step S42, a process of analyzing the detection results obtained by the process of the measurement operation program and calculating analysis results is executed. The details of this process are shown in FIG. 20.

In step S43, a process of allowing display 3 to display analysis result screen (dog) 37a (FIG. 14) or analysis result screen 37b (FIG. 15) including the analysis results calculated in step S42 is executed.

In step S44, a process of allowing display 3 to display main screen 31 (FIG. 3) is executed when a predetermined period of time passes after the process of step S43.

In step S45, an error process is executed. The error process is a process of allowing display 3 to display a message stating that the measurement has not normally ended.

In step S46, a process of setting the start flag to be "0" is executed.

With reference to FIG. 18, the contents of the mid-initial-measurement screen displaying process in step S21 will be described.

FIG. 18 is a flowchart showing the details of the mid-initial-measurement screen display processing routine.

In step S61, a process of preparing an initial screen in area 21a of memory 21 is executed.

Figure 21:
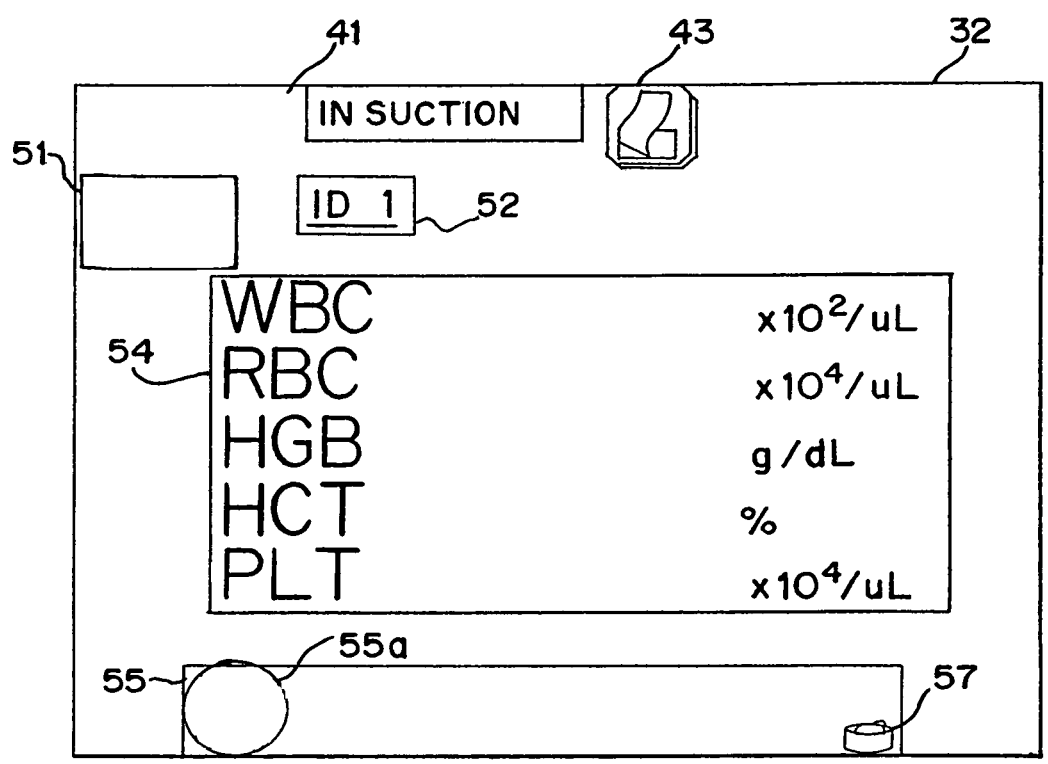
FIG. 21 is a view describing an initial screen.

With reference to FIG. 21, the initial screen will be described. Initial screen 32 includes apparatus state display area 41, a print commanding area 43, a measurement mode display area 51, a specimen number display area 52, an analysis result display area 54, and a progression display area 55.

Measurement mode display area 51 is blank. Progression display area 55 currently includes only food picture 57.

Returning to FIG. 18, the mid-initial-measurement screen display processing routine will be described.

In step S62, a process of determining whether the dog flag is "1" or not is executed. If the dog flag is "1", the procedure goes to step-S63, while if the dog flag is not "1", the procedure goes to step S64.

In step S63, a process of adding dog picture 51a to area 51 of initial screen 32 (FIG. 21) and adding dog picture 56a to position 55a is executed. By this process, mid-initial-measurement screen (dog) 32a (FIG. 4) is prepared.

In step S64, a process of determining whether the cat flag is "1" or not is executed. If the cat flag is "1", the procedure goes to step S65, while if the cat flag is not "1", the procedure goes to step S66.

In step S65, a process of adding cat picture 51b to area 51 of initial screen 32 and adding cat picture 56b to position 55a is executed. By this process, mid-initial-measurement screen (cat) 32b (FIG. 5) is prepared.

In step S66, a process of allowing display 3 to display the prepared mid-initial-measurement screen (dog) 32a or mid-initial-measurement screen (cat) 32b is executed.

With reference to FIG. 19, the contents of the measurement operation program started in step S22 will be described.

FIG. 19 is a flowchart schematically and generally showing the process executed by the measurement operation program.

In step S71, a process of setting the LV0 flag to be "1", and setting the LV1 flag, LV2 flag, suction-completed flag, and measurement-end flag to be "0" is executed.

In step S72, a process of giving commands for allowing suction mechanism 16 to suck the specimen is executed.

In step S73, a process of setting the LV0 flag to be "0" and setting the suction-completed flag to be "1" is executed after suction mechanism 16 has finished sucking the specimen.

In step S74, a process of giving commands for allowing specimen suction mechanism 16 and fluid controlling section 8 to prepare a sample, i.e. processes such as dilution of the specimen and hemolysis, is executed.

In step S75, a process of setting the suction-completed flag to be "0" and setting the LV1 flag to be "1" is executed after the preparation of the sample has been finished.

In step S76, a process of giving commands for allowing detection section 17 to detect an electric signal from the sample is executed.

In step S77, a process of setting the LV1 flag to be "0" and setting the LV2 flag to be "1" is executed when a predetermined period of time passes after the start of the commands of step S76.

In step S78, a process of allowing A/D conversion circuit 24 to perform digital conversion of the electric signal detected by detection section 17 and writing the obtained detection results into area 21d of memory 21 is executed.

In step S79, a process of setting the LV2 flag to be "0" and setting the measurement-end flag to be "1" is executed after the writing process of step S78 is finished.

With reference to FIG. 20, the contents of the analysis process in step S42 will be described.

FIG. 20 is a flowchart showing the details of the analysis processing routine.

In step S91, a process of calculating the number of red blood cells, the number of white blood cells, the hematocrit value, and the like from the detection results stored in area 21d of memory 21 is executed.

In step S92, a process of determining whether the dog flag is "1" or not is executed. If the dog flag is "1", the procedure goes to step S93, while if the dog flag is not "1", the procedure goes to step S94.

In step S93, a process of correcting the calculation results obtained in step S91 in accordance with the characteristics of dog blood is executed. In this process, a process, for example, of multiplying the obtained hematocrit value by 0.97 is executed.

In step S94, a process of determining whether the cat flag is "1" or not is executed. If the cat flag is "1", the procedure goes to step S95, while if the cat flag is not "1", the procedure goes to step S43 (FIG. 17).

In step S95, a process of correcting the calculation results obtained in step S91 in accordance with the characteristics of cat blood is executed. In this process, a process, for example, of multiplying the obtained hematocrit value by 0.88 is executed.

The analyzer according to the above-described embodiment displays a picture of an animal that a user feels attached to during the measurement operation, so that the user does not feel displeased even if the measurement operation requires a long period of time.

Further, in the analyzer according to the above-described embodiment, there is a change in the display of display 3 during the measurement operation, so that the user does not get tired even if the measurement takes a long period of time.

Here, the analyzer according to the above-described embodiment may be constructed to include a sound source (cry generator) in controlling substrate section 9 so that the sound source may generate a dog cry in the dog measurement mode and a cat cry in the cat measurement mode. For example, if the dog mode is selected in step S43 (FIG. 17), the sound source may generate a dog cry, while if the cat mode is selected, the sound source may generate a cat cry. For example, a speaker and a micro computer that memorizes predetermined program for generating cries may be used as the sound source.

This provides that, even if the user is not looking at display 3, the user can recognize, by the cry, that the analysis results have been displayed, and can confirm the selected measurement mode.

In other words, by constructing blood analyzer 1 in this manner, the user can understand the progression of the measurement even if the user is not looking at display 3.

Further, in step S6 (FIG. 16), the sound source may generate a dog cry while the flags are set; and, in step S8, the sound source may generate a cat cry while the flags are set. In this case, data corresponding to the dog cry and the cat cry may be stored in memory 21. This provides that the user can grasp that a measurement mode has been selected and confirm the selected measurement mode with the cry.

Further, in step S4, the sound source may generate a cry of an animal corresponding to the selected measurement mode while the flags are set. This provides that the user can confirm the measurement mode selected at the start of the measurement. Furthermore, the user can grasp that the measurement has been started even if the user is not looking at display 3.

Here, the sound source may be a sound source that records cries in advance, or may be a sound source that generates cries by combination of electronic sounds.

Further, the analyzer according to the above-described embodiment may display dog picture 51a or cat picture 51b on main screen 31 in accordance with the selected measurement mode. For example, in step S6 (FIG. 16), dog picture 51a may be displayed in an area between print commanding area 43 and start button display area 50 of main screen 31 while the dog flag and cat flag are set; and, in step S8, cat picture 51b may be displayed in an area between print commanding area 43 and start button display area 50 of main screen 31 while the dog flag and cat flag are set. This provides that, on main screen 31, dog picture 51a is displayed if the dog measurement mode is selected, and cat picture 51b is displayed if the cat measurement mode is selected. Therefore, the user can confirm the selected measurement mode before the start of the measurement, thereby preventing start of the measurement in a wrong measurement mode.

In addition, the analyzer according to the above-described embodiment may change pictures displayed on display 3 in accordance with the progression of the measurement operation. For example, a picture of a dog in a sleeping state may be displayed in step S21 (FIG. 17); a picture of a dog in a state of being asleep but having a raised head may be displayed in step S27; a picture of a dog in a sitting state may be displayed in step S34; and a picture of a dog in a standing state may be displayed in step S39. In this case, the dog picture may be displayed at the same position of the screen, or may be displayed by changing positions.

In addition, the analyzer according to the above-described embodiment may display letters on display 3 in accordance with the progression of the measurement operation. For example, the letters "bowwow" may be displayed in step S21 (FIG. 17); the letters "bowwow bowwow" may be displayed in step S27; the letters "bowwow bowwow bowwow" may be displayed in step S34; and the letters "bowwow bowwow bowwow bowwow" may be displayed in step S39.

Further, the analyzer according to the above-described embodiment may display a message showing that the measurement operation has been finished. For example, in step S39 (FIG. 17), the letters "measurement ended" may be displayed.

Further, the analyzer according to the above-described embodiment may display a message showing the period of time until the end of the measurement. For example, in step S34 (FIG. 17) the letters "one minute till the end of measurement" may be displayed.

By constructing blood analyzer 1 in this manner, the user can easily understand how long it will take until the measurement is finished.

The present invention is not limited to the above-described embodiment. For example, the present invention may be applied to a blood analyzer capable of analyzing blood of an animal other than dog or cat. Further, this invention can be applied to various blood analyzer such as a blood analyzer capable of operating in a mode for measuring diluted blood and in a mode for measuring non-diluted blood. Further, this invention can be applied to various analyzer such as a urine analyzer.

Further, though in the above-described embodiment an analyzer in which a measurement mechanism and a display are integrated has been described; however, the present invention is not limited thereto. The present invention can be applied to an analyzer in which an analyzer main body having a measurement mechanism mounted thereon and a personal computer are connected with a connection cable. In this case, the aforesaid application program may be stored in the personal computer, and the measurement operation program may be stored in the analyzer main body.

What is claimed is:

1. An analyzer configured for operating in a plurality of measurement modes, comprising:
    a measurement device for capturing a signal from an analyte by performing a measurement operation;
    a display for displaying at least one screen; and
    a controller in communication with the measurement device and the display, the controller comprising a processor and a non-transitory memory under control of the processor,
    wherein the non-transitory memory stores a plurality of pictures, each of the pictures being associated with one of the plurality of measurement modes,
    wherein the processor is programmed to carry out operations comprising:
        detecting an input selecting one measurement mode from the plurality of measurement modes, wherein the plurality of measurement modes comprises a first measurement mode for analyzing a first analyte from a first kind of animal and a second measurement mode for analyzing a second analyte from a second kind of animal, and wherein the first kind and the second kind are different;
        detecting an input starting the measurement operation;
        displaying on the at least one screen a picture associated with the selected measurement mode when the input starting the measurement operation has been detected, wherein a first picture associated with the first measurement mode is displayed if the input selecting the first measurement mode has been detected and a second picture associated with the second measurement mode is displayed if the input selecting the second measurement mode has been detected;
        performing the measurement operation by the measurement device;
        analyzing the signal captured by the measurement device; and
        displaying an analysis result of the signal.

2. The analyzer of claim 1, wherein the processor is further programmed for selecting a picture associated with the selected measurement mode from the plurality of pictures stored in the non-transitory memory.

3. The analyzer of claim 2, wherein the processor is further programmed for the displaying of the picture by displaying the picture associated with the selected measurement mode in a first area on a first screen.

4. The analyzer of claim 3, wherein the processor is further programmed for the displaying of the picture by displaying the picture associated with the selected measurement mode in a second area on the first screen.

5. The analyzer of claim 3, wherein the processor is further programmed for the displaying of the picture by displaying the picture associated with the selected measurement mode at different positions in the first area on the first screen in accordance with a progression of the measurement operation.

6. The analyzer of claim 1, wherein the non-transitory memory further stores an end notification picture for notifying a user that a measurement operation is ended, and wherein the processor is further programmed for displaying the end notification picture after the measurement operation has ended.

7. The analyzer of claim 1 wherein the measurement device comprises a suction mechanism configured to suck an analyte from a removable specimen container, and wherein the processor is further programmed for detecting completion of analyte suction by the suction mechanism from the removable specimen container, and providing a message notification that the removable specimen container can be removed upon detection of suction completion.

8. An analyzer configured for operating in a plurality of measurement modes, comprising:
a measurement device for capturing a signal from an analyte by performing a measurement operation;
a display; and
a controller in communication with the measurement device and the display, the controller comprising a processor and a non-transitory memory under control of the processor,
wherein the non-transitory memory stores a plurality of pictures, each of the pictures being associated with one of the plurality of measurement modes,
wherein the processor is programmed to carry out operations comprising:
detecting an input selecting one measurement mode from the plurality of measurement modes;
performing the measurement operation by the measurement device;
displaying a picture associated with the selected measurement mode during the measurement operation, wherein a first picture associated with the first measurement mode is displayed if the input selecting the first measurement mode has been detected and a second picture associated with the second measurement mode is displayed if the input selecting the second measurement mode has been detected;
changing a position of the displayed picture in accordance with a progression of the measurement operation;
analyzing the signal captured by the measurement device; and
displaying an analysis result of the signal.

9. The analyzer of claim 8, wherein the processor is further programmed for changing a form of the displayed picture in accordance with a progression of the measurement operation.

10. An analyzer configured for operating in a plurality of measurement modes, comprising:
a measurement device for capturing a signal from an analyte by performing a measurement operation;
a display for displaying at least one screen; and
a controller in communication with the measurement device and the display, the controller comprising a processor and a non-transitory memory under control of the processor,
wherein the non-transitory memory stores a plurality of pictures, each of the pictures being associated with one of the plurality of measurement modes,
wherein the processor is programmed to carry out operations comprising:
detecting an input selecting one measurement mode from the plurality of measurement modes, wherein the plurality of measurement modes comprises a first measurement mode for analyzing a first analyte from a first kind of animal and a second measurement mode for analyzing a second analyte from a second kind of animal, and wherein the first kind and the second kind are different;
detecting an input starting the measurement operation;
displaying on at least one mid-measurement screen a picture associated with the selected measurement mode after the measurement operation has been started, wherein a first picture associated with the first measurement mode is displayed if the input selecting the first measurement mode has been detected and a second picture associated with the second measurement mode is displayed if the input selecting the second measurement mode has been detected;
performing the measurement operation by the measurement device;
analyzing the signal captured by the measurement device; and
displaying on an analysis result screen an analysis result of the signal.

11. The analyzer of claim 10, wherein the processor is further programmed for displaying on a main screen at least one selection area for receiving the input selecting one measurement mode from the plurality of measurement modes and a start button area for receiving the input starting the measurement operation.

12. The analyzer of claim 10, wherein the at least one mid-measurement screen includes an analysis result display area, a measurement mode display area, and a progression display area, wherein the processor is further programmed for the displaying on the at least one mid-measurement screen by displaying the picture associated with the selected measurement mode in the measurement mode display area and the progression display area.

13. The analyzer of claim 12, wherein the processor is further programmed for the displaying on the at least one mid-measurement screen by changing a position of the picture associated with the selected measurement mode that is displayed in the progression display area in accordance with a progression of the measurement operation.

14. The analyzer of claim 10, wherein the analysis result screen includes a measurement mode display area and an analysis result display area, wherein the processor is further programmed for the displaying on the analysis result screen by displaying the picture associated with the selected measurement mode in the measurement mode display area and displaying the analysis result of the signal in the analysis result display area.

15. The analyzer of claim 10, wherein the non-transitory memory further stores an end notification picture for notifying a user that the measurement operation is ended, and wherein the processor is further programmed for displaying the end notification picture on the at least one mid-measurement screen after the measurement operation has ended.

16. The analyzer of claim 10 wherein the measurement device comprises a suction mechanism configured to suck an analyte from a removable specimen container, and wherein the processor is further programmed for detecting completion of analyte suction by the suction mechanism from the removable specimen container, and providing a message notification on the at least one mid-measurement screen that the removable specimen container can be removed upon detection of suction completion.

* * * * *